United States Patent
Liu et al.

(10) Patent No.: US 9,546,197 B2
(45) Date of Patent: Jan. 17, 2017

(54) METHOD FOR PREPARING CYCLIC LIPOPEPTIDE COMPOUND

(75) Inventors: Shidong Liu, Shanghai (CN); Zhaoli Zhang, Shanghai (CN); Yi Chen, Shanghai (CN); Xiusheng Wang, Shanghai (CN); Liangliang Zhou, Shanghai (CN); Xiaoming Ji, Shanghai (CN)

(73) Assignee: Shanghai Techwell Biopharmaceutical Co., Ltd., Shanghai (CN)

( * ) Notice: Subject to any disclaimer, the term of this patent is extended or adjusted under 35 U.S.C. 154(b) by 266 days.

(21) Appl. No.: 13/982,797

(22) PCT Filed: Jan. 31, 2012

(86) PCT No.: PCT/CN2012/070783
§ 371 (c)(1),
(2), (4) Date: Nov. 13, 2013

(87) PCT Pub. No.: WO2012/103800
PCT Pub. Date: Aug. 9, 2012

(65) Prior Publication Data
US 2014/0057320 A1    Feb. 27, 2014

(30) Foreign Application Priority Data

Jan. 31, 2011  (CN) .......................... 2011 1 0034243

(51) Int. Cl.
*C07K 7/54*    (2006.01)
*C07K 7/56*    (2006.01)
*C12N 1/14*    (2006.01)
*C12R 1/645*   (2006.01)
*C12P 7/64*    (2006.01)

(52) U.S. Cl.
CPC . *C07K 7/54* (2013.01); *C07K 7/56* (2013.01); *C12N 1/14* (2013.01); *C12P 7/64* (2013.01); *C12R 1/645* (2013.01)

(58) Field of Classification Search
None
See application file for complete search history.

(56) References Cited

U.S. PATENT DOCUMENTS 5,376,634 A * 12/1994 Iwamoto et al. ............. 514/3.3
2010/0239711 A1* 9/2010 Li ............................ A23F 5/02
426/45

FOREIGN PATENT DOCUMENTS

CN    1059729 A    3/1992

OTHER PUBLICATIONS

Iwamoto et al., WF11899 A, B and C, novel antifungal lipopeptides: I. Taxonomy, fermentation, isolation and physico-chemical properties, Journal of Antibiotics, vol. 47, Issue 10, Oct. 1994, pp. 1084-1091.*
International Search Report for PCT/CN2012/070783 dated Apr. 5, 2012.
Kanda et al., "Improvement of FR901379 Production by Mutant Selection and Medium Optimization," Journal of Bioscience and Bioengineering, vol. 107, No. 5, 530-534, 2009.
Hashimoto, Seiji, "Micafungin: a Sulfated Echinocandin," The Journal of Antibiotics (2009), 62, 27-35.
Kanda et al., "Scale-Up Fermentation of Echinocandin Type Antibiotic FR901379," Journal of Bioscience and Bioengineering, vol. 109, No. 2, 138-144, 2010.

* cited by examiner

*Primary Examiner* — Karen Cochrane Carlson
*Assistant Examiner* — Jennifer M. H. Tichy
(74) *Attorney, Agent, or Firm* — Hamre, Schumann, Mueller & Larson, P.C.

(57) ABSTRACT

Provided is a method for preparing a compound represented by Formula I or a salt thereof, wherein *Coleophoma empetri* F-11899 (FERM BP2635) and/or a mutant strain thereof is cultured in a medium containing amino acid or a salt thereof, an insoluble organic source, and a sugar alcohol, to produce the compound of Formula I or a salt thereof.

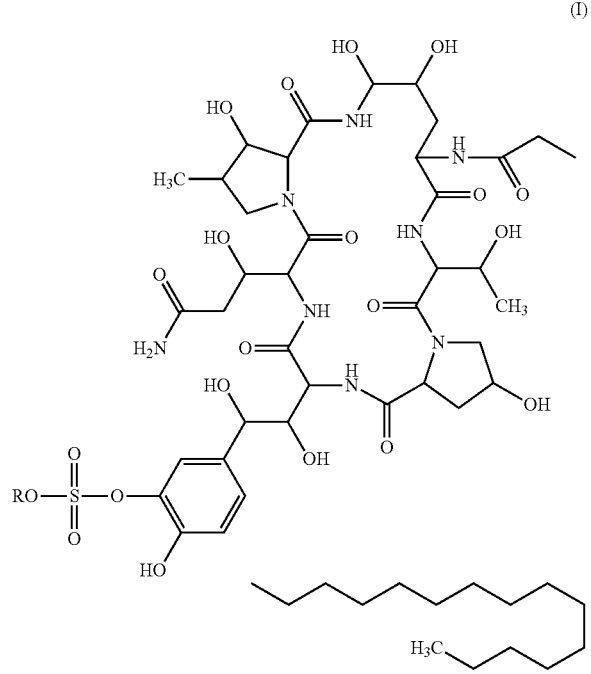

9 Claims, No Drawings

METHOD FOR PREPARING CYCLIC LIPOPEPTIDE COMPOUND

This application is a U.S. National Phase Patent Application of PCT/CN2012/070783 filed on Jan. 31, 2012, which was published under WO/2012/013800, which claims priority to Chinese Patent Application No. 201110034243.3 filed on Jan. 31, 2011.

FIELD OF THE INVENTION

The present invention relates to the method for biosynthesizing cyclic lipopeptide compound biologically, in particular, to the method for preparing the compound of Formula I through bio-fermentation.

BACKGROUND OF THE INVENTION

Fungus infections have become the major cause for the high morbidity and mortality in immunodeficiency patients. During the past 20 years, the incidence of mycotic infection has increased significantly. The high-risk population for the fungus infection includes critical patients, surgical patients and the patients with HIV-infection, leukemia as well as other tumors. Additionally, the organ transplant recipients are also the high-risk population for fungus infection.

Echinocandins, as a kind of novel anti-fungal medicaments, are effective in treating *Candida-* or *aspergillus-* infections, and the examples of which are Caspofungin and Micafungin. The echinocandins inhibit the fungi by inhibiting the formation of 1,3-β glucosidic bond, thereby reducing the toxicity toward the human and the side effects, while maintaining high efficiency. Therefore, compared with the traditional anti-fungal medicaments, the echinocandins are safer when they are used.

FK463 (Micafungin) is the compound of Formula III, which is obtained by removing the side-chain of compound FR901379 of Formula I through enzymolysis for forming compound FR179642 of Formula II, and then chemically modifying compound FR179642. Therefore, the production of compound of Formula I obtained through fermentation is very important for obtaining Micafungin.

However, the production for the compound of Formula I through fermentation maintains at low level for a long time. Great efforts have been made for seeking a medium with low-cost and high-production, but little progress has been made, therefore it is more difficult to prepare the compound of Formula I, thus increasing the cost and price for FK463. Therefore, it is urgent to find a method for synthesizing the compound of Formula I with low cost and high efficiency.

Fujisawa Pharmaceutical Co Ltd (Japan) has obtained A-3 medium by replacing corn starch with soluble starch to reduce the viscosity of medium upon sterilization and adding sulfate and phosphate to control pH during the fermentation (Improvement of FR901379 production by mutant selection and medium optimization, Journal of Bioscience and Bioengineering, VOL 107 No. 5, 530-534, 2009). Afterwards, Fujisawa further improved A-3 medium by adding high concentration of ammonium sulfate to reduce the viscosity and replacing cottonseed meal with corn steep liquid, thereby obtaining medium A-4 for higher production of the compound of Formula I (Scale-up fermentation of echinocandin type antibiotic FR901379, Journal of Bioscience and Bioengineering, VOL 109 No. 2, 138-144, 2010).

However, it is necessary to further increase the production of compound of Formula I. And the viscosity of the above medium is still very high, and the mycelia form pellet during the fermentation, all of which are adverse to the dissolved oxygen control and subsequent filtering operation.

The inventors found a medium for increasing the production of compound of Formula I through creative works and great amount of experiments. Using the medium in the fermentation, the viscosity of the culture is low, the dissolved oxygen can be readily controlled and the mycelia won't form pellet.

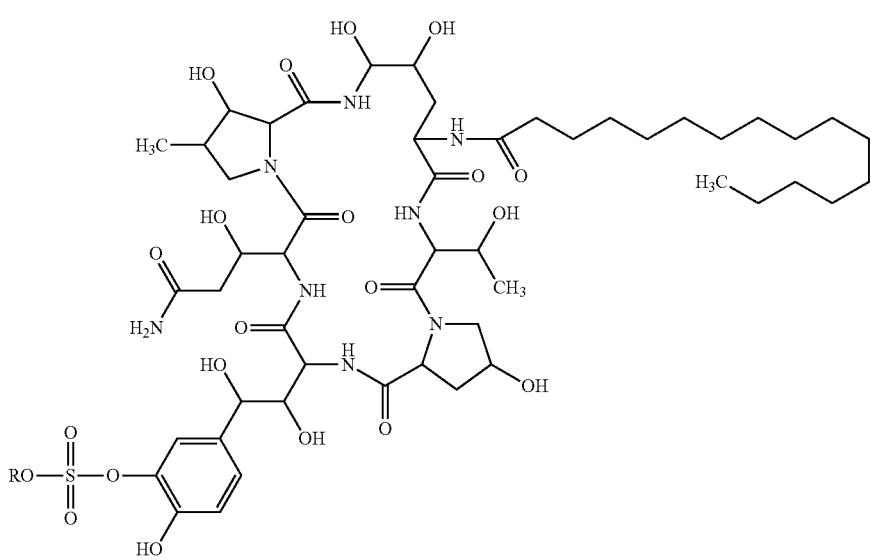

(the compound of Formula I)

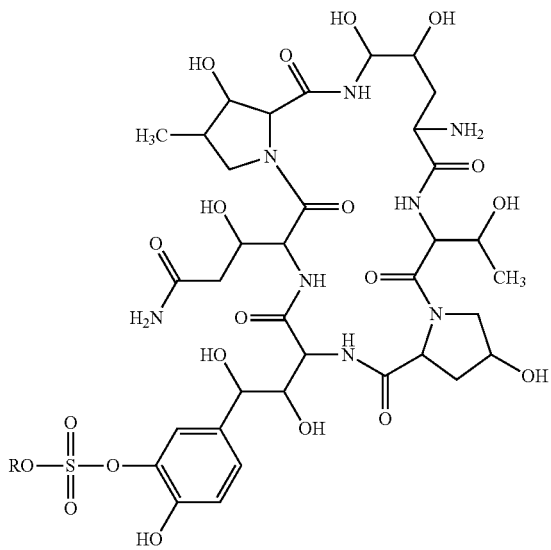

II

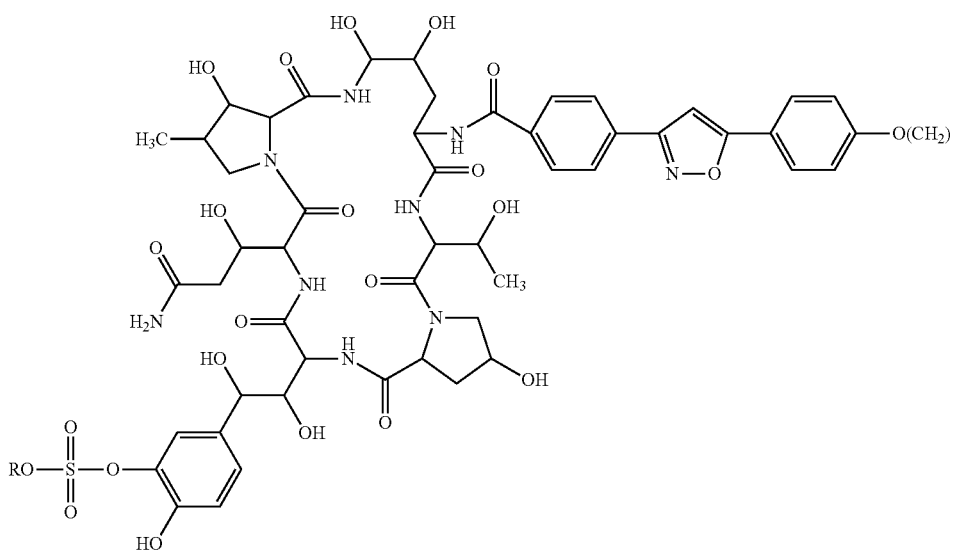

III (Micafungin)

SUMMARY OF THE INVENTION

The technical problem to be resolved by the present invention is to provide a medium for the strain suitable for producing the compound of Formula I through fermentation, thereby increasing the production of compound of Formula I.

For achieving the above purpose, the inventors firstly used small molecule organic compounds as carbon source to greatly reduce the viscosity of the medium in shake flasks, and determined the types and contents of the carbon source in the present invention through optimization experiments. Regarding the potential precursors, the inventors have added various amino acids or the salts thereof into the medium for increasing the production of compound of Formula I, and have determined the types and contents of amino acids or the salts thereof through optimization experiments. Additionally, yeast extract and various trace metal ions have been added into the medium for providing trace elements and growth factors necessary for the growth of mycelium. Through the above improvements, the ability of the strain to produce the compound of Formula I in the flasks has been greatly increased, the viscosity of the medium is very low, and the mycelium is readily to be filtered.

When the above medium is applied to 50 L fermentation, the strain can not grow normally, small amount of mycelia is obtained, the mycelia tend to form pellets, and the production of compound of Formula I is low. Upon exclusion of the reasons, such as inoculation amount, dissolved oxygen and shear stress produced by agitation and the like, the inventors resolved the problem by adding insoluble organic nitrogen sources. And then, the types and contents of the organic nitrogen source in the present invention have been further determined through optimization experiments.

Through the above further improvements to the medium, the ability of the strain for producing the compound of Formula I has been greatly increased in 50 L fermentation system, the viscosity of the medium is very low, and the mycelium is readily to be filtered. The inventors further applied the above medium to 3000 L fermentation system, and obtained the same results.

The strain used in the present invention is *Coleophoma empetri* F-11899 (FERM BP2635), and the strains obtained by mutagenesis, for example (but not limited to), the strain described in CN201010587865.4, which has been deposited at the Chinese Culture Collection Committee General Microbiology Center in Beijing under the accession number CGMCC 4129 based on Budapest Treaty since Aug. 31, 2010. The strain *Coleophoma empetri* F-11899 has been deposited in Fermentation Research Institute Agency of Industrial Science and Technology (1-3, Higashi 1 chome, Tsukuba-shi, IBARAKI 305 JAPAN) since Oct. 26, 1989 under the number of FERM BP2635.

The present invention has been completed based on *Coleophoma empetri* F-11899 (FERM BP2635) by the inventors, and the medium is also suitable for many mutagenized strains.

The following material are necessarily contained in the medium for preparing the compound of Formula I:
(1) amino acids or the salts thereof;
(2) insoluble organic nitrogen source;
(3) sugar alcohol.

It is necessarily to comprise amino acids or the salts thereof in the medium. Said amino acid can be one or more selected from the following group consisting of glutamic acid, proline, ornithine, threonine or the salts thereof; and preferably, said amino acid is sodium glutamate, or proline. The best effects can be reached when the concentration of amino acid in the medium is 0.5-5.0 wt %.

It is necessarily to comprise, in part, insoluble organic nitrogen source in the medium. Said organic nitrogen source can be one or more selected from the following group consisting of soybean meal, soy protein isolate, groundnut meal, cottonseed meal, and soybean cake meal; and preferably, said organic nitrogen source is the granular insoluble nitrogen source, such as cottonseed meal, soybean cake meal, and groundnut meal, and the like. The best effects can be reached when the concentration of organic nitrogen source in the medium is 0.5-3.0 wt %.

It is necessarily to comprise sugar alcohol in the medium as carbon source. Said sugar alcohol can be one or more selected from the following group consisting of glycerin (glycerol), erythritol, xylitol, ribitol, arabitol, sorbitol, mannitol and galactitol; and preferably, said sugar alcohol is hexitol, such as sorbitol, mannitol and galactitol, and the like. The best effects can be reached when the concentration of sugar alcohol in the medium is 1.0-10.0 wt %, more preferably, 2.0-8.0 wt %.

The medium according to the invention further comprises certain amount of other basic substances, such as yeast extract, magnesium salts, sulfate and other trace elements, and the like.

In a preferred example of the invention, sugar alcohol and amino acids or the salts thereof are further supplemented during the culture of the strain.

Sugar alcohol and amino acids or the salts thereof are preferably supplemented at 40-80$^{th}$ hr during the culture. The amount of supplemented sugar alcohol is 0.5%-3% per day, and the amount of supplemented amino acids or the salts thereof is 0.1%-1% per day based on the volume of the initial culture. The specific time and amount for feeding are determined according to the content of sugar alcohol and amino acids or the salts thereof in the initial medium: if the content in the initial medium is high, the time for feeding can be appropriately retarded, and the amount for feeding can be appropriately reduced; and if the content in the initial medium is low, the time for feeding can be appropriately advanced, and the amount for feeding can be appropriately increased.

Regarding the seed medium and control of part of the process parameters used in the invention, reference can be made to Scale-up fermentation of echinocandin type antibiotic FR901379 Journal of Bioscience and Bioengineering, VOL 109 No. 2, 138-144, 2010 for the culture method of seed and the control of the process parameters during fermentation.

The main advantages of the present invention include:

1. A medium for greatly increasing the fermentation titer of compound of Formula I is provided by the invention. Since the titer of compound of Formula I has been increased, the amount of organic solvent used in the process of extraction and post-treatment as well as the damage to the environment can be reduced;

2. A medium for greatly reducing the viscosity of fermentation culture and improving the growth morphology of the strain is provided by the invention. Since the viscosity of medium is low and the growth morphology of mycelia is improved, the dissolved oxygen during the fermentation is readily controlled and the mycelia are readily filtered upon fermentation, thereby reducing the energy consumption and production cost;

3. The production of compound of Formula I can be greatly increased by the invention, thereby reducing the production cost of subsequent compounds of Formula II and III, and facilitating the industrial production of compound of Formula I and the popularization of compound of Formula III.

MODES FOR CARRYING OUT THE INVENTION

Using conventional means for optimizing the fermentation medium, the inventors have obtained a medium suitable for producing the compound of Formula I through fermentation, upon a great deal of experiments. Thus, the inventors accomplished the present invention based on such medium.

As used herein, "compound of Formula I" and "Formula I compound" can be used interchangeably, both referring to the compound having the following structure or the pharmaceutically acceptable salts thereof:

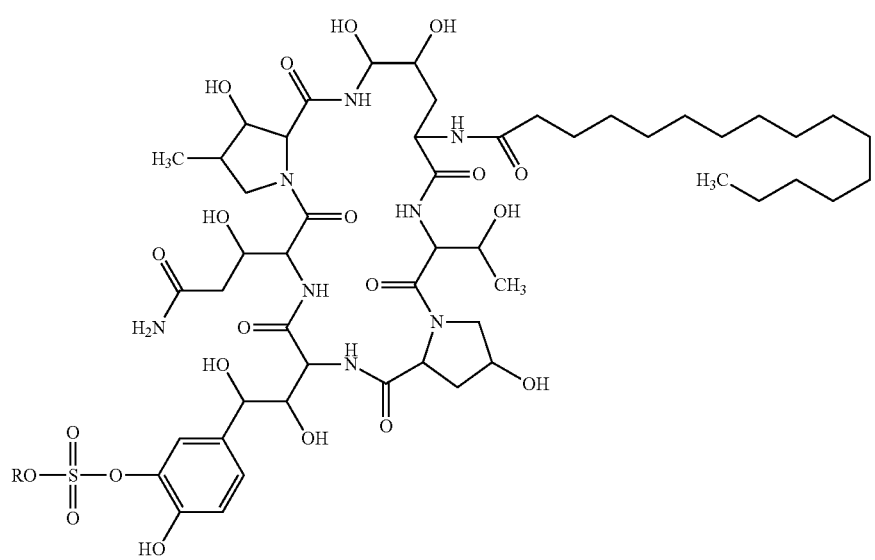

Wherein, R represents H or pharmaceutically acceptable cations capable of forming addition-salts.

Preferably, "pharmaceutically acceptable salts" include the metal salts, such as alkali metal salts (such as sodium salts, potassium salts), alkaline earth metal salts (such as calcium salts, magnesium salts, and the like), ammonium salt, salt formed with organic base (such as trimethylamine salt, triethylamine salt, pyridinium salt, methylpyridine salt, dicyclohexyl ammonium salt, N,N'-dibenzylethylenediamine), organic acid-addition salts (such as formate, acetate, trifluoroacetate, maleate, tartrate, methylsulfonate, benzene sulfonate, tosylate, and the like), inorganic acid-addition salts (such as hydrochloride, hydrobromide, hydroiodate, sulfate, phosphate, and the like), and salts formed with amino acids (such as arginine, aspartic acid, glutamic acid, and the like).

The strain used in the present invention is *Coleophoma empetri* F-11899 (FERM BP2635), and the strains obtained by mutagenesis, for example (but not limited to), the strain described in CN201010587865.4, the deposit number of which is CGMCC 4129.

The production method of the invention is the same as that reported in the art for preparing the compound of Formula I, except for the mutation-bred strain and fermentation conditions, for example, the extraction and purification process for compound of Formula I.

With respect to the fermentation conditions for preparing the compound of Formula I, it is necessary to comprise yeast extract, magnesium salts, sulfates and other trace elements and the like, in addition to the above essential nutrient elements, such as amino acids, insoluble organic nitrogen source and sugar alcohol. The fermentation can be conducted under pH 5.5-6.5 (preferably, pH 5.7-6.2) and the temperature of 20° C.-30° C. (preferably, 23° C.-28° C.).

Some preferred medium are listed as follows:

Slant medium is potato dextrose agar (PDA) consisting of: potato 30%, dextrose 2%, agar 1.5%.

The formulation described in Scale-up fermentation of echinocandin type antibiotic FR901379, Journal of Bioscience and Bioengineering, VOL 109 No. 2, 138-144, 2010 is used as the seed medium, which consists of: sucrose 1%, cottonseed meal 2%, dry yeast 1%, peptone 1%, $KH_2PO_4$ 0.2%, $CaCO_3$ 0.2%, defoaming agent 0.05%.

The formulation described in Scale-up fermentation of echinocandin type antibiotic FR901379 Journal of Bioscience and Bioengineering, VOL 109 No. 2, 138-144, 2010 is used as the fermentation medium (used in Comparative Example), which consists of: soluble starch 12%, rice bran oil 3%, corn steep liquid 4%, $(NH_4)_2SO_4$ 1%, $KH_2PO_4$ 0.5%, $MgSO_4 \cdot 7H_2O$ 0.2%, Adekanol LG-109 0.05%.

The composition of fermentation medium used in the present invention is: amino acids or the salts thereof (preferably, sodium glutamate, proline) 0.5-5.0 wt %, insoluble organic nitrogen source (preferably, soybean cake meal, cottonseed meal, groundnut meal) 0.5-3.0 wt %, sugar alcohol (preferably, sorbitol, mannitol, and galactitol) 2.0-8.0 wt %, $(NH_4)_2SO_4$ 0.1-1.0%, $KH_2PO_4$ 0.1-0.5 wt %, $MgSO_4 \cdot 7H_2O$ 0.02-0.2 wt %, trace elements 1.0-2.0 wt %, defoaming agent 0.05 wt %.

Trace elements: $FeSO_4 \cdot 7H_2O$ 10 g/L, $MnSO_4 \cdot H_2O$ 10 g/L, $ZnSO_4 \cdot 7H_2O$ 2 g/L, $CaCl_2$ 0.7 g/L, $H_3BO_3$ 0.56 g/L, $CuCl_2 \cdot 2H_2O$ 0.25 g/L, $(NH_4)_6Mo_7O_{24} \cdot 7H_2O$ 0.19 g/L, concentrated hydrochloric acid 500 ml/L.

A preferred process for producing the compound of Formula I through fermentation is described as follows:

At 25° C., strain *Coleophoma empetri* F-11899 (FERM BP2635) or the mutagenized strain CGMCC 4129 is cultured on slant for 6-10 days, mature mycelia or spores are inoculated into the seed medium, and then cultured on a shaking table at 280 rpm under 25° C. for 2-4 days.

2-10% of seed culture is inoculated into the fermentation medium, and cultured at 23-28° C. on an automatic fermentor with pH being maintained at 5.7-6.2. After the mycelia are cultured for 3-6 days, 1-6% of carbon source (sugar alcohol, starch) and 1-4% of nitrogen (amino acids, such as proline, glutamic acid, threonine, and the like) is supplemented daily, and the culture is generally performed for 8-12 days.

The method for determining the compound of Formula I is described as follows:

Certain volume of fermentation liquid is obtained, 2 volumes of methanol is added, and the resulting mixture is agitated for extracting the compound of Formula I. The mycelia are removed by centrifugation, and the content of compound of Formula I in the extract is determined by HPLC external standard method.

The HPLC method for determining the compound of Formula I used in Examples is described as follows:

The analysis is performed on Waters analytic HPLC system. FR901379, Pneumocandin B0 and other analogues are determined by reverse phase HPLC analysis. The conditions for reverse phase HPLC analysis is listed as follows:

CALESIL ODS chromatographic column (particle size 5 μm, 4.6 mmi. d×250 mm);

Temperature: 35° C.;

mobile phase: 50% acetonitrile/0.5% aqueous ammonium dihydrogen phosphate;

flow rate: 1.0 mL/min;

detection wavelength: 210 nm.

The method for determining the viscosity of fermentation liquid belongs to the well-known method in the art, for example, using Brookfield viscometer.

The present invention will be further illustrated below with reference to specific examples. It should be understood that these examples are only to illustrate the present invention but not to limit the scope of the present invention. The experimental methods with no specific conditions described in the following examples are generally performed under conventional conditions or according to the manufacture's instruction. Unless indicated otherwise, all of the percentages, ratios, proportions, or parts are calculated by weight.

The unit of the weight to volume percentage used in the present invention is well known to those skilled in the art, for example, it refers to the weight of solute in a 100 milliliter of solution.

Unless otherwise defined, all the technical and scientific terms used in the present specification have the meanings as commonly understood by those skilled in the art. In addition, all of the methods and materials which are similar or equivalent with the contents disclosed herein can be applied in the present methods. The preferred methods and materials for carrying out the present methods described herein are only given as examples.

EXAMPLE 1

Preparation of Seed Liquid of *Coleophoma empetri* F-11899 (FERM BP2635) for Fermentation The seed liquid of *Coleophoma empetri* F-11899(FERM BP2635) was prepared according to the method described in Scale-up fermentation of echinocandin type antibiotic FR901379, Journal of Bioscience and Bioengineering, VOL 109 No. 2, 138-144, 2010 for the subsequent production of compound of Formula I.

Slant medium was potato dextrose agar (PDA) consisting of: potato 30%, dextrose 2%, agar 1.5%.

The seed medium consisted of: sucrose 1%, cottonseed meal 2%, dry yeast 1%, peptone 1%, $KH_2PO_4$ 0.2%, $CaCO_3$ 0.2%, defoaming agent 0.05%.

At 25° C., strain *Coleophoma empetri* F-11899 (FERM BP2635) was cultured on the slant for 6-10 days, mature mycelia or spores were inoculated into the seed medium, and then cultured on a shaking table at 280 rpm under 25° C. for 2-4 days.

EXAMPLE 2

Preparation of Seed Liquid of Mutagenized Strain CGMCC 4129 for Fermentation

The seed liquid of mutagenized strain CGMCC 4129 was prepared according to the method described in Scale-up fermentation of echinocandin type antibiotic FR901379, Journal of Bioscience and Bioengineering, VOL 109 No. 2, 138-144, 2010 for the subsequent production of compound of Formula I.

Slant medium was potato dextrose agar (PDA) consisting of: potato 30%, dextrose 2%, agar 1.5%.

The seed medium consisted of: sucrose 1%, cottonseed meal 2%, dry yeast 1%, peptone 1%, $KH_2PO_4$ 0.2%, $CaCO_3$ 0.2%, defoaming agent 0.05%.

At 25° C., strain GMCC 4129 was cultured on the slant for 6-10 days, mature mycelia or spores were inoculated into the seed medium, and then cultured on a shaking table at 280 rpm under 25° C. for 2-4 days.

EXAMPLE 3

Preparation of Compound of Formula I

Into a 250 mL flask, 50 ml of medium comprising mannitol 5%, yeast extract 0.5%, L-proline 1%, cottonseed meal 1%, ammonium sulfate 0.1%, magnesium sulfate 0.06%, solution of trace element 0.1%, and MES 2% was added. pH of the medium was adjusted to 5.5±0.5, and the medium was sterilized at 121° C. for 30 mins. The seed obtained in Example 1 (1 ml) was seeded into the medium at an inoculation amount of 2%, and cultured at the temperature of 25° C., 280 rpm for 240 hours. The culture was sampled for analysis, and the viscosity of the final culture was 2200 cp, and the content of compound of Formula I was 0.5 g/L.

Trace elements: $FeSO_4 \cdot 7H_2O$ 10 g/L, $MnSO_4 \cdot H_2O$ 10 g/L, $ZnSO_4 \cdot 7H_2O$ 2 g/L, $CaCl_2$ 0.7 g/L, $H_3BO_3$ 0.56 g/L, $CuCl_2 \cdot 2H_2O$ 0.25 g/L, $(NH_4)_6Mo_7O_{24} \cdot 7H_2O$ 0.19 g/L, concentrated hydrochloric acid 500 ml/L.

EXAMPLE 4

Preparation of Compound of Formula I

Into a 250 mL flask, 50 ml of medium comprising mannitol 4%, sodium glutamate 1%, threonine 0.8%, soybean cake meal 2%, yeast extract 0.8%, ammonium sulfate 0.2%, magnesium sulfate 0.05%, solution of trace element 0.1%, and MES 2.5% was added. pH of the medium was adjusted to 5.5±0.5, and the medium was sterilized at 121° C. for 30 mins. The seed obtained in Example 2 (1 ml) was seeded into the medium at an inoculation amount of 2%, and cultured at the temperature of 25° C., 280 rpm for 240 hours. The culture was sampled for analysis, and the viscosity of the final culture was 2300 cp, and the content of compound of Formula I was 1.94 g/L.

Trace elements: $FeSO_4 \cdot 7H_2O$ 10 g/L, $MnSO_4H_2O$ 10 g/L, $ZnSO_4 \cdot 7H_2O$ 2 g/L, $CaCl_2$ 0.7 g/L, $H_3BO_3$ 0.56 g/L, $CuCl_2 \cdot 2H_2O$ 0.25 g/L, $(NH_4)_6Mo_7O_{24} \cdot 7H_2O$ 0.19 g/L, concentrated hydrochloric acid 500 ml/L.

EXAMPLE 5

Preparation of Compound of Formula I

Into a 50 L fermentor, 29 L of tap water, 600 g soybean cake meal (2%), 2400 g mannitol (8%), 600 g L-proline (2%), 240 g of yeast extract (0.8%), 30 g of ammonium sulfate (0.1%), 12 g of magnesium sulfate (0.04%), and 30 ml of solution of trace element (0.1%), were added. pH of the medium was adjusted to 5.5±0.5 using sodium hydroxide or hydrochloric acid, and the medium was sterilized at 121° C. for 30 mins. The seed obtained in Example 1 (0.9 L) was seeded into the medium at an inoculation amount of 3%, thereby obtaining 30 L of culture. Aeration rate was controlled at 1-2 vvm, dissolved oxygen was controlled at no less than 80%, pH was controlled at 6.0±0.5, and the culture temperature was controlled at 25±5° C. After 60 hours, mannitol (1%) and L-proline (0.5%) were supplemented daily, based on the volume of initial culture (30 L). The fermentation was terminated at 240$^{th}$ hour. The culture was sampled for analysis, the viscosity of the final culture was 4500 cp, and the content of compound of Formula I was 0.5 g/L.

Trace elements: $FeSO_4.7H_2O$ 10 g/L, $MnSO_4.H_2O$ 10 g/L, $ZnSO_4.7H_2O$ 2 g/L, $CaCl_2$ 0.7 g/L, $H_3BO_3$ 0.56 g/L, $CuCl_2.2H_2O$ 0.25 g/L, $(NH_4)_6Mo_7O_{24}.7H_2O$ 0.19 g/L, concentrated hydrochloric acid 500 ml/L.

EXAMPLE 6

Preparation of Compound of Formula I

Into a 50 L fermentor, 29 L of tap water, 150 g soybean cake meal (0.5%), 300 g mannitol (1%), 750 g L-proline (2.5%), 750 g of sodium glutamate (2.5%), 240 g of yeast extract (0.8%), 30 g of ammonium sulfate (0.1%), 12 g of magnesium sulfate (0.04%), and 30 ml of solution of trace element (0.1%), were added. pH of the medium was adjusted to 5.5±0.5 using sodium hydroxide or hydrochloric acid, and the medium was sterilized at 121° C. for 30 mins. The seed obtained in Example 1 (0.9 L) was seeded into the medium at an inoculation amount of 3%, thereby obtaining 30 L of culture. Aeration rate was controlled at 1-2 vvm, dissolved oxygen was controlled at no less than 80%, pH was controlled at 6.0±0.5, and the culture temperature was controlled at 25±5° C. After 40 hours, mannitol (1.5%) and L-proline (0.8%) were supplemented daily, based on the volume of initial culture (30 L). The fermentation was terminated at 240$^{th}$ hour. The culture was sampled for analysis, the viscosity of the final culture was 2300 cp, and the content of compound of Formula I was 0.43 g/L.

EXAMPLE 7

Preparation of Compound of Formula I

Into a 50 L fermentor, 29 L of tap water, 900 g soybean cake meal (3.0%), 3000 g mannitol (10%), 150 g L-proline (0.5%), 30 g of threonine (0.1%), 240 g of yeast extract (0.8%), 30 g of ammonium sulfate (0.1%), 12 g of magnesium sulfate (0.04%), and 30 ml of solution of trace element (0.1%), were added. pH of the medium was adjusted to 5.5±0.5 using sodium hydroxide or hydrochloric acid, and the medium was sterilized at 121° C. for 30 mins. The seed obtained in Example 1 (0.9 L) was seeded into the medium at an inoculation amount of 3%, thereby obtaining 30 L of culture. Aeration rate was controlled at 1-2 vvm, dissolved oxygen was controlled at no less than 80%, pH was controlled at 6.0±0.5, and the culture temperature was controlled at 25±5° C. After 80 hours, mannitol (0.5%) and L-proline (1%) were supplemented daily, based on the volume of initial culture (30 L). The fermentation was terminated at 240$^{th}$ hour. The culture was sampled for analysis, the viscosity of the final culture was 2600 cp, and the content of compound of Formula I was 0.44 g/L.

Trace elements: $FeSO_4.7H_2O$ 10 g/L, $MnSO_4.H_2O$ 10 g/L, $ZnSO_4.7H_2O$ 2 g/L, $CaCl_2$ 0.7 g/L, $H_3BO_3$ 0.56 g/L, $CuCl_2.2H_2O$ 0.25 g/L, $(NH_4)_6Mo_7O_{24}.7H_2O$ 0.19 g/L, concentrated hydrochloric acid 500 ml/L.

EXAMPLE 8

Preparation of Compound of Formula I

Into a 50 L fermentor, 29 L of tap water, 300 g cottonseed meal (1.0%), 2400 g mannitol (8%), 900 g sodium glutamate (3.0%), 300 g of threonine (1.0%), 240 g of yeast extract (0.8%), 30 g of ammonium sulfate (0.1%), 12 g of magnesium sulfate (0.04%), and 30 ml of solution of trace element (0.1%), were added. pH of the medium was adjusted to 5.5±0.5 using sodium hydroxide or hydrochloric acid, and the medium was sterilized at 121° C. for 30 mins. The seed for compound of Formula I obtained in Example 1 (0.9 L) was seeded into the medium at an inoculation amount of 3%, thereby obtaining 30 L of culture. Aeration rate was controlled at 1-2 vvm, dissolved oxygen was controlled at no less than 80%, pH was controlled at 6.0±0.5, and the culture temperature was controlled at 25±5° C. After 60 hours, mannitol (1%) and threonine (0.3%) were supplemented daily, based on the volume of initial culture (30 L). The fermentation was terminated at 240$^{th}$ hour. The culture was sampled for analysis, the viscosity of the final culture was 2100 cp, and the content of compound of Formula I was 0.58 g/L.

Trace elements: $FeSO_4.7H_2O$ 10 g/L, $MnSO_4.H_2O$ 10 g/L, $ZnSO_4.7H_2O$ 2 g/L, $CaCl_2$ 0.7 g/L, $H_3BO_3$ 0.56 g/L, $CuCl_2.2H_2O$ 0.25 g/L, $(NH_4)_6Mo_7O_{24}.7H_2O$ 0.19 g/L, concentrated hydrochloric acid 500 ml/L.

EXAMPLE 9

Preparation of Compound of Formula I

Into a 50 L fermentor, 29 L of tap water, 600 g groundnut meal (2.0%), 600 g mannitol (2%), 600 g L-proline (2.0%), 240 g of yeast extract (0.8%), 30 g of ammonium sulfate (0.1%), 12 g of magnesium sulfate (0.04%), and 30 ml of solution of trace element (0.1%), were added. pH of the medium was adjusted to 5.5±0.5 using sodium hydroxide or hydrochloric acid, and the medium was sterilized at 121° C. for 30 mins. The seed obtained in Example 1 (0.9 L) was seeded into the medium at an inoculation amount of 3%, thereby obtaining 30 L of culture. Aeration rate was controlled at 1-2 vvm, dissolved oxygen was controlled at no less than 80%, pH was controlled at 6.0±0.3, and the culture temperature was controlled at 25±2° C. After 50 hours, mannitol (3%) and L-proline (0.5%) were supplemented daily, based on the volume of initial culture (30 L). The fermentation was terminated at 240$^{th}$ hour. The culture was sampled for analysis, the viscosity of the final culture was 2900 cp, and the content of compound of Formula I was 0.52 g/L.

Trace elements: $FeSO_4.7H_2O$ 10 g/L, $MnSO_4.H_2O$ 10 g/L, $ZnSO_4.7H_2O$ 2 g/L, $CaCl_2$ 0.7 g/L, $H_3BO_3$ 0.56 g/L, $CuCl_2.2H_2O$ 0.25 g/L, $(NH_4)_6Mo_7O_{24}.7H_2O$ 0.19 g/L, concentrated hydrochloric acid 500 ml/L.

EXAMPLE 10

Preparation of Compound of Formula I

Into a 50 L fermentor, 29 L of tap water, 600 g cottonseed meal (2.0%), 1800 g mannitol (6%), 600 g L-proline (2.0%), 240 g of yeast extract (0.8%), 30 g of ammonium sulfate (0.1%), 12 g of magnesium sulfate (0.04%), and 30 ml of solution of trace element (0.1%), were added. pH of the medium was adjusted to 5.5±0.5 using sodium hydroxide or hydrochloric acid, and the medium was sterilized at 121° C. for 30 mins. The seed liquid obtained in Example 2 (0.9 L) was seeded into the medium at an inoculation amount of 3%, thereby obtaining 30 L of culture. Aeration rate was controlled at 1-2 vvm, dissolved oxygen was controlled at no less than 80%, pH was controlled at 6.0±0.5, and the culture temperature was controlled at 25±2° C. After 50 hours, mannitol (1%) and L-proline (0.5%) were supplemented daily, based on the volume of initial culture (30 L). The fermentation was terminated at 240$^{th}$ hour. The culture was sampled for analysis, the viscosity of the final culture was 2300 cp, and the content of compound of Formula I was 2.5 g/L.

Trace elements: FeSO$_4$.7H$_2$O 10 g/L, MnSO$_4$.H$_2$O 10 g/L, ZnSO$_4$.7H$_2$O 2 g/L, CaCl$_2$ 0.7 g/L, H$_3$BO$_3$ 0.56 g/L, CuCl$_2$.2H$_2$O 0.25 g/L, (NH$_4$)$_6$Mo$_7$O$_{24}$.7H$_2$O 0.19 g/L, concentrated hydrochloric acid 500 ml/L.

EXAMPLE 11

Preparation of Compound of Formula I

Into a 50 L fermentor, 29 L of tap water, 300 g cottonseed meal (1%), 2400 g sorbitol (8%), 600 g L-proline (2.0%), 120 g of yeast extract (0.4%), 30 g of ammonium sulfate (0.1%), 30 g of magnesium sulfate (0.1%), and 30 ml of solution of trace element (0.1%), were added. pH of the medium was adjusted to 5.5±0.5 using sodium hydroxide or hydrochloric acid, and the medium was sterilized at 121° C. for 30 mins. The seed liquid obtained in Example 2 (0.9 L) was seeded into the medium at an inoculation amount of 3%, thereby obtaining 30 L of culture. Aeration rate was controlled at 1-2 vvm, dissolved oxygen was controlled at no less than 80%, pH was controlled at 6.0±0.5, and the culture temperature was controlled at 25±2° C. After 70 hours, sorbitol (1%) and L-proline (0.5%) were supplemented daily, based on the volume of initial culture (30 L). The fermentation was terminated at 240$^{th}$ hour. The culture was sampled for analysis, the viscosity of the final culture was 2300 cp, and the content of compound of Formula I was 2.0 g/L.

Trace elements: FeSO$_4$.7H$_2$O 10 g/L, MnSO$_4$.H$_2$O 10 g/L, ZnSO$_4$.7H$_2$O 2 g/L, CaCl$_2$ 0.7 g/L, H$_3$BO$_3$ 0.56 g/L, CuCl$_2$.2H$_2$O 0.25 g/L, (NH$_4$)$_6$Mo$_7$O$_{24}$.7H$_2$O 0.19 g/L, concentrated hydrochloric acid 500 ml/L.

EXAMPLE 12

Preparation of Compound of Formula I

Into a 50 L fermentor, 29 L of tap water, 600 g cottonseed meal (2%), 2400 g galactitol (8%), 300 g sodium glutamate (1.0%), 120 g of yeast extract (0.4%), 60 g of ammonium sulfate (0.1%), 15 g of magnesium sulfate (0.05%), and 30 ml of solution of trace element (0.1%), were added. pH of the medium was adjusted to 5.5±0.5 using sodium hydroxide or hydrochloric acid, and the medium was sterilized at 121° C. for 30 mins. The seed liquid obtained in Example 2 (0.9 L) was seeded into the medium at an inoculation amount of 3%, thereby obtaining 30 L of culture. Aeration rate was controlled at 1-2 vvm, dissolved oxygen was controlled at no less than 80%, pH was controlled at 6.0±0.5, and the culture temperature was controlled at 25±2° C. After 60 hours, galactitol (1%) and sodium glutamate (0.5%) were supplemented daily, based on the volume of initial culture (30 L). The fermentation was terminated at 240$^{th}$ hour. The culture was sampled for analysis, the viscosity of the final culture was 2600 cp, and the content of compound of Formula I was 1.8 g/L.

COMPARATIVE EXAMPLE 1

In a 50 L fermentor, *Coleophoma empetri* F-11899 (FERM BP2635) and the mutagenized strain CGMCC 4129 were respectively cultured according to the fermentation methods for compound of Formula I described in Scale-up fermentation of echinocandin type antibiotic FR901379, Journal of Bioscience and Bioengineering, VOL 109 No. 2, 138-144, 2010. In the resulting final culture, viscosity is 11000 cp and 9800 cp respectively, and the content of compound of Formula I is 0.2 g/L and 1.4 g/L respectively.

COMPARATIVE EXAMPLE 2

In a 50 L fermentor, *Coleophoma empetri* F-11899 (FERM BP2635) and the mutagenized strain CGMCC 4129 were respectively cultured according to the fermentation method for compound of Formula I described in Example 1 of EP0431350B1. In the resulting final culture, viscosity is 10500 cp and 9400 cp respectively, and the content of compound of Formula I is 0.14 g/L and 1.2 g/L respectively.

The above description is merely the preferred examples of the present invention, and is not intended to limit the scope of the substantial technical contents of the present invention. The substantial technical contents of the present invention are broadly defined in the scope of the claims appended to the present application. Any technical entity or method accomplished by others should be deemed as falling into the scope of the claims of the present application if the entity or method is completely identical with that defined in the claims of the present application or an equivalent change or modification thereof.

The invention claimed is:

1. A method of preparing a compound of formula I or a salt thereof comprises the following step:
    culturing a strain *Coleophoma empetri* F-11899 (FERM BP2635) or a mutagenized strain thereof in a fermentation medium comprising an amino acid or a salt thereof, an insoluble organic nitrogen source, and a sugar alcohol as a carbon source to obtain said compound of formula 1 or the salt thereof,

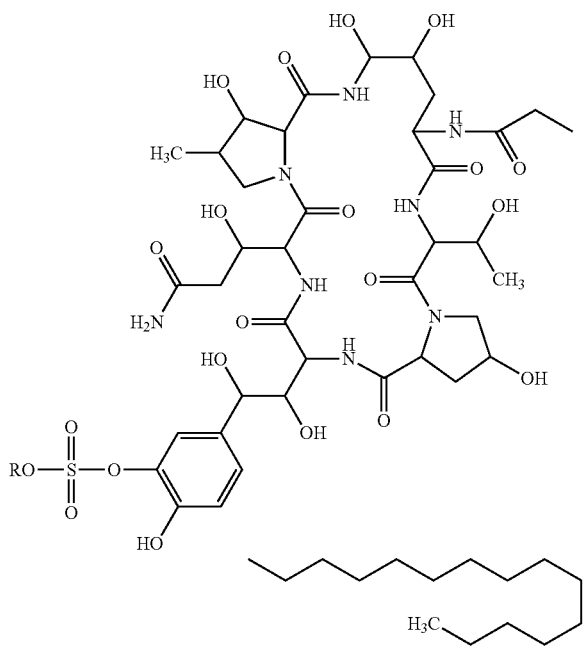

(I)

wherein said amino acid includes proline or threonine or salts thereof,
said insoluble organic nitrogen source is one or more selected from the group consisting of soybean meal, soy protein isolate, groundnut meal, cottonseed meal, and soybean cake meal, and
said sugar alcohol includes sorbitol or mannitol.

2. The method of claim 1, wherein a concentration of said amino acid or the salt thereof is 0.5-5.0 wt %, based on a total weight of the fermentation medium.

3. The method of claim 1, wherein a concentration of said insoluble organic nitrogen source is 0.5-3.0 wt %, based on a total weight of the fermentation medium.

4. The method of claim 1, wherein a concentration of said sugar alcohol is 1.0-10.0 wt %, based on a total weight of the fermentation medium.

5. The method of claim 1, wherein said strain is cultured at a temperature of 20° C.-30° C. and a pH value of 5.5-6.5.

6. The method of claim 1, wherein said sugar alcohol and said amino acid or the salt thereof are supplemented during the culturing of said strain.

7. The method of claim 6, wherein said sugar alcohol and said amino acid or the salt thereof are supplemented at about 40-80$^{th}$ hour during the culturing.

8. The method of claim 6, wherein said sugar alcohol is supplemented in an amount of 0.5%-3% per day, and said amino acid or the salt thereof is supplemented in an amount of 0.1%-1% per day, based on a volume of an initial culture.

9. The method of claim 7, wherein said sugar alcohol is supplemented in an amount of 0.5%-3% per day, and said amino acid or the salt thereof is supplemented in an amount of 0.1%-1% per day, based on a volume of an initial culture.

* * * * *